Figure 1A:
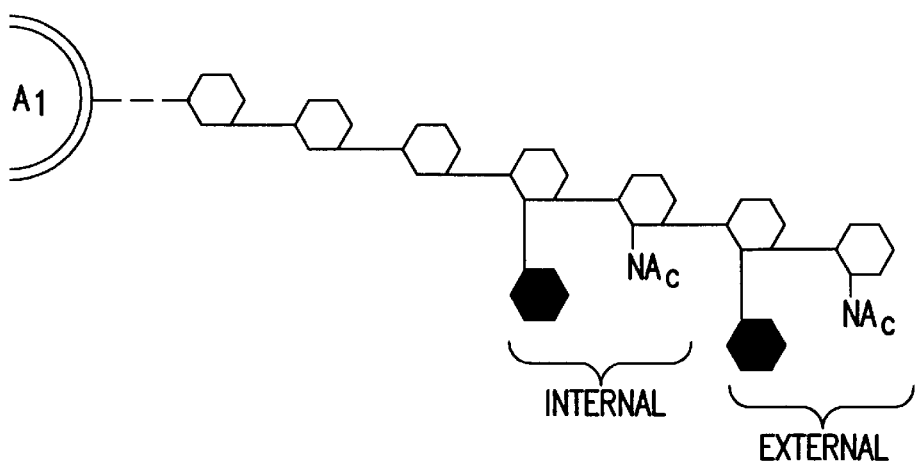
Figure 1B:
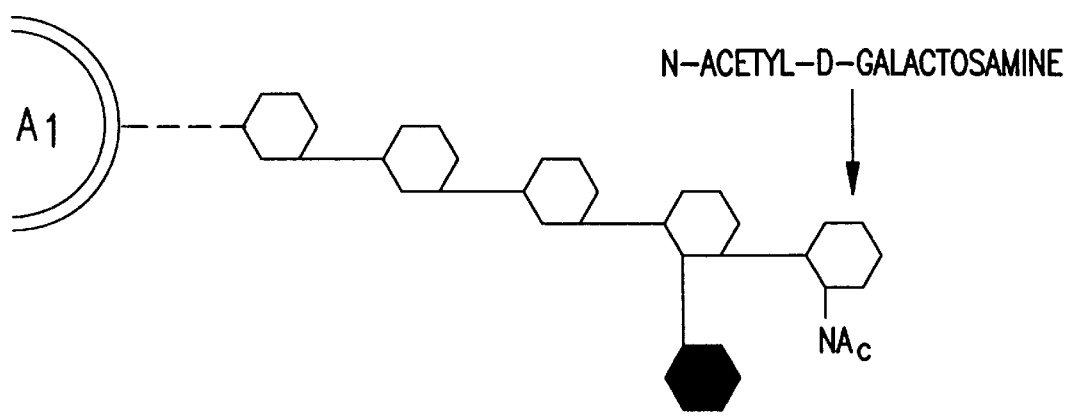

United States Patent [19]
Goldstein et al.

[11] Patent Number: 5,925,541
[45] Date of Patent: Jul. 20, 1999

[54] ENDO-β-GALACTOSIDASE

[75] Inventors: Jack Goldstein; Alex Zhu; Lin Leng, all of New York, N.Y.

[73] Assignee: New York Blood Center, Inc., New York, N.Y.

[21] Appl. No.: 08/712,072

[22] Filed: Sep. 11, 1996

[51] Int. Cl.$^6$ ..................................................... C12P 21/06
[52] U.S. Cl. .................................. 435/69.1; 435/252.33; 435/320.1; 530/350
[58] Field of Search .................. 424/93.73; 435/207, 435/252.33, 254.11, 69.1, 71.1, 71.2, 320.1, 325; 536/23.2; 530/350

[56] References Cited

U.S. PATENT DOCUMENTS 4,609,627  9/1986  Goldstein ................................ 435/269

OTHER PUBLICATIONS

Fukuda, 1995, Current Protocols in Molecular Biology, Suppl. 32, John Wiley & Sons, §§ 17.17.6–17.17.13.
Zhu and Goldstein, 1993, Gene 137:309–314.
Amano et al., 1991, J. Biol. Chem. 266:11461–11477.
Goldstein, 1989, Transfusion Medicine Reviews (III)3:206–212.
Scudder et al., 1983, Biochem J. 213:485–494.
Fukuda, 1981, J. Biol. Chem. 256:3900–3905.
Kitamikado, 1981, J. Biol. Chem. 256:3906–3909.
Nakasawa and Suzuki, 1975, J. Biol. Chem. 250:912–917.
Hirano and Meyer, 1971, Biochem. Biophys. Res. Commun. 44:1371–1375.

*Primary Examiner*—James Ketter
*Assistant Examiner*—Irem Yucel
*Attorney, Agent, or Firm*—Amster, Rothstein & Ebenstein

[57] ABSTRACT

The present invention relates to purified and isolated nucleic acid encoding the endo-β-galactosidase from *Flavobacterium keratolyticus* (referred to as "ENDO-A"), and to purified ENDO-A protein. The endo-β-galactosidase of the invention may be used in a process which enzymatically de-antigenizes human erythrocytes bearing $A_1$ antigen. The resulting erythrocytes may be transfused into individuals who would be otherwise unable to tolerate a transfusion of type $A_1$ blood.

16 Claims, 10 Drawing Sheets

```
                                ED-11
  1     AT TAG GCA GCT TGC TCC ACA AGC CGT CAA ATA ACG ATA TAA ACT TAA
                                    ───────►
 48     ATA GAA CCA ATA ATC CAA AAC TAA ATG AGA AAA ACC AAA TTT TGG CTG
  1                                     M   R   K   T   K   F   W   L

96     GTG CTG AGC CTA ATC GCA ACT AGC CTG TCT ATT TTT GCC TGC AAA AAA
  9      V   L   S   L   I   A   T   S   L   S   I   F   A   C   K   K

144     GAC TCT ACA GCA ACA AAA AAT CCG ATT CCG GAA GTA AGT AAG GCG AAG
 25      D   S   T   A   T   K   N   P   I   P   E   V   S   K   A   K
                                                              ED-1*
192     GCA TCG ACT AAG CTA TTA AAT GCG ACT ACC GTA GCG ACA ACA GAC TAC
 41      A   S   T   K   L   L   N   A   T   T   V   A   T   T   D   Y
              ED-2*         pep-1
240     GAA TTG ATC TGG TCG GAT GAG TTT AAT AGT AGT GGG GGA TTT GAT TCC
 57      E   L   I   W   S   D   E   F   N   S   S   G   G   F   D   S
                                    ED-5
288     ACA AAA TGG TCT TAT GCT GAC AGG GGC ACT GTC GCA TGG AAT AAG TAT
 73      T   K   W   S   Y   A   D   R   G   T   V   A   W   N   K   Y
             ED-6
336     ATG ACC TCC TTG CCG GCT TAT GCA TCC CAA GAT GGG AGC AAT CTC GTA
 89      M   T   S   L   P   A   Y   A   S   Q   D   G   S   N   L   V
                 ED-7
                             ED-3*                        ED-8    ED-4*
384     TTG CGT ATG GAT AAT GCA GTT GTA GCC GGG GAT CCT GTT GCC TAT CAT
105      L   R   M   D   N   A   V   V   A   G   D   P   V   A   Y   H
                     pep-2
432     GCT GGA GGA GTT AAG TCG ATG GGG AAA TTT AGT ATG ACT TAT GGA AAA
121      A   G   G   V   K   S   M   G   K   F   S   M   T   Y   G   K
                                    pep-3           pep-4
480     GTT GAA GTG AGG GCT AAA TTT ACA CAA GGA AGA GGT TCA TGG CCT GCT
137      V   E   V   R   A   K   F   T   Q   G   R   G   S   W   P   A 528     ATT TGG ATG ATG CCT GAA CCA GCT ACA GCG TAC GGC GGC TGG CCT AGC
153      I   W   M   M   P   E   P   A   T   A   Y   G   G   W   P   S
                     pep-5                                      ED-13
576     TGT GGT GAA ATT GAC AGT ATG GAG CAT GTC AAC AAC GAA AGT GTG ATG
169      C   G   E   I   D   S   M   E   H   V   N   N   E   S   V   M
                                    pep-6
624     TAC CAT ACG ATC CAT AAT GGC TCA GTT ACC AAT GCA AAT GGT GGG AGC
185      Y   H   T   I   H   N   G   S   V   T   N   A   N   G   G   S
        pep-7
672     ACA GCA TCG AAA TCT GCC ACC TAT AAT ACG ACA GAT TAC AAC CTA TAT
201      T   A   S   K   S   A   T   Y   N   T   T   D   Y   N   L   Y
```

FIG.2A

```
720  ACG ATG ATC TGG AGT CCG AAC GAC ATT CGA TTC TAC GTC AAC AAT TCA
217   T   M   I   W   S   P   N   D   I   R   F   Y   V   N   N   S
                                    ED-9
768  TTG CAG TAT ACC TAC GCA AGA GTT TCC GGT GGG GGG ACA CAG CAA TGG
233   L   Q   Y   T   Y   A   R   V   S   G   G   G   T   Q   Q   W

816  CCA TTT GAC GTT CCT TTT TAT CTG ATT CTA AAT CAG GCC GGT GGA GCG
249   P   F   D   V   P   F   Y   L   I   L   N   Q   A   G   G   A

864  GGA TGG CCA GGG GCG ATC ACA AAT GCT GAC TTG CCC TTT AGT ATG CAG
265   G   W   P   G   A   I   T   N   A   D   L   P   F   S   M   Q

912  GTG GAT TAC GTG CGT GTA TAT AAG CTG CCT TTA TTT AGT AAT GGC GAT
281   V   D   Y   V   R   V   Y   K   L   P   L   F   S   N   G   D

960  TTC GAA AGC GGT GTC ATC TAT CCA TGG ACA ACA TGG GGC GGT GGA TCA
297   F   E   S   G   V   I   Y   P   W   T   T   W   G   G   G   S

1008 TCG GTT GTT TCC ACC GAT GCC CGG ACA GGA ACC AAA TGC ATC CGC GAA
313   S   V   V   S   T   D   A   R   T   G   T   K   C   I   R   E

1056 ACA GGC GGA GAG ACA TCC ATT GAA CAA TAC CTG ACC GGT TTA ACG CCA
329   T   G   G   E   T   S   I   E   Q   Y   L   T   G   L   T   P

1104 AAT ACG ACC TAT CGG TTC GGT GGC TAC GCC AAA GTG TCT GCA GCT GGC
345   N   T   T   Y   R   F   G   G   Y   A   K   V   S   A   A   G

1152 CAA TCA GTC AGT ATT GGT GTC AAA AAT TAT GGG GGA ACT GCG GTC GAT
361   Q   S   V   S   I   G   V   K   N   Y   G   G   T   A   V   D
     ED-10
1200 GCG ACT ATA GGT ACG ACC AGC TAC TCC AAT AAT TCG GTA ACT TTT ACA
377   A   T   I   G   T   T   S   Y   S   N   N   S   V   T   F   T

1248 ACT GGA GCC AAT AAT ACT ACT GCT ACG GTC TAT TTC TAT AAA CCC TTG
393   T   G   A   N   N   T   T   A   T   V   Y   F   Y   K   P   L

1269 AGC GGT ACA GTG TAT GGT GAT GAT TTC TAT TTG GAA AAA TTG TAA AAC
409   S   G   T   V   Y   G   D   D   F   Y   L   E   K   L   *
                                                                ED-12
1344 ACC GTA GTT AGA AGA GCA GCG GTT TAG TTC AAC CGC TGC TCT TTT AGC
1392 AAT ACT GCG TGA TGA CG
```

FIG.2B

```
e13b    361           375 376           390 391           405 406           420 421           435 436           450
        FQPIQENMQIRIGYP LNGQAGGNIGNNFVN YTFIGNPNAPRPDVS DQEDISIGTPTDPAI AGMNLTWQDEFNGTT L-DTSKWNYHIGYYL   44
gub     ------KMMRRTAFL LS------------- -VLIG CSMLGS---- ----DRS DK----- -------A PHWELVWSDEFDYSG LPDPEKWDYDVGGHG    6
endo-gal ------KAKA-STKL LN------------- -------AT TVATTD- --------------- -------- --YELIWSDEFNSSG GFDSTKWSYADRGTV    8 e13b    451           465 466           480 481           495 496           510 511           535 536           540
        NNDPATWGWGNAELQ HYTNS-TQNVYVQDC KLNIKAMNDSKSFPQ DPNRYAQYSSGKINT KDNLSLKYGRVDFRA KLPTGDCVWPALWML   53
gub     -------WGNQELQ YYTRARIENARVGGG VLIIEAR-------- ------H EPYEGREYTSARLVT RGNASWTYGRFEIRA RLPSGRGTWPAIWML   14
endo-gal ----AWN------ -KYMTSLP AYASQDGSNLVLRMD NAVVAGD------- ----PVAYHAGGVKS MGNFSMTYGKVEVRA KFTQGRGSWPAIWMM   15 e13b    541           555 556           570 571           585 586           600 601           615 616           630
        PK-DSVYG--TWAAS GEIDVMEARGRLPGS VSGTIHFGGQWPVNQ SS-GGDYHFPEGGQTF ANDYHVYSVVWEEDN IKWYVDGKFFYKVTN   62
gub     PD-RQTYGSAYWPDN GEIDIMEHVGFNPDV VHGTVHTKAYNHLLG TQRGGSIRVP----TA RTDFHVIAIEWTPEE IRWFVDDSLYRFPN   22
endo-gal PEPATAYG--GWPSC GEIDSMEHVN-NESV MYHTIHNGSVTNANG GS-TASKSAT----TN TTDYNLYTMIWSPND IRFYVNNSLQYTYAR   23 e13b    631           645 646           660 661           675 676           690 691           705 706           720
        QQWYSTAAPNNPNAP FDEPFYLIMNLAVGG NFDGGRTPNASDIPA TMQVDYVRVYKHQ-- --------------- ---------------   68
gub     ERLTDPEADWR-HWP FDQPFHLIMNIAVGG AWGGQQGVDPEAFPA QLVVDYVRVYRHVE- --------------- ---------------   28
endo-gal ------VSGGGTQQWP FDVPFYLILNQAGGA GWPG--AITNADLPF SMQVDYVRVYKIPLF SMGDFESGVIYPWTT WGGGSSVVSTDARTG   32
```

FIG. 4

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1408 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
ATTAGGCAGC TTGCTCCACA AGCCGTCAAA TAACGATATA AACTTAAATA GAACCAATAA      60

TCCAAAACTA AATGAGAAAA ACCAAATTTT GGCTGGTGCT GAGCCTAATC GCAACTAGCC     120

TGTCTATTTT TGCCTGCAAA AAAGACTCTA CAGCAACAAA AAATCCGATT CCGGAAGTAA     180

GTAAGGCGAA GGCATCGACT AAGCTATTAA ATGCGACTAC CGTAGCGACA ACAGACTACG     240
```

```
AATTGATCTG GTCGGATGAG TTTAATAGTA GTGGGGGATT TGATTCCACA AAATGGTCTT    300

ATGCTGACAG GGGCACTGTC GCATGGAATA AGTATATGAC CTCCTTGCCG GCTTATGCAT    360

CCCAAGATGG GAGCAATCTC GTATTGCGTA TGGATAATGC AGTTGTAGCC GGGGATCCTG    420

TTGCCTATCA TGCTGGAGGA GTTAAGTCGA TGGGGAAATT TAGTATGACT TATGGAAAAG    480

TTGAAGTGAG GGCTAAATTT ACACAAGGAA GAGGTTCATG GCCTGCTATT TGGATGATGC    540

CTGAACCAGC TACAGCGTAC GGCGGCTGGC CTAGCTGTGG TGAAATTGAC AGTATGGAGC    600

ATGTCAACAA CGAAAGTGTG ATGTACCATA CGATCCATAA TGGCTCAGTT ACCAATGCAA    660

ATGGTGGGAG CACAGCATCG AAATCTGCCA CCTATAATAC GACAGATTAC AACCTATATA    720

CGATGATCTG GAGTCCGAAC GACATTCGAT TCTACGTCAA CAATTCATTG CAGTATACCT    780

ACGCAAGAGT TTCCGGTGGG GGGACACAGC AATGGCCATT TGACGTTCCT TTTTATCTGA    840

TTCTAAATCA GGCCGGTGGA GCGGGATGGC CAGGGGCGAT CACAAATGCT GACTTGCCCT    900

TTAGTATGCA GGTGGATTAC GTGCGTGTAT ATAAGCTGCC TTTATTTAGT AATGGCGATT    960

TCGAAAGCGG TGTCATCTAT CCATGGACAA CATGGGGCGG TGGATCATCG GTTGTTTCCA   1020

CCGATGCCCG GACAGGAACC AAATGCATCC GCGAAACAGG CGGAGAGACA TCCATTGAAC   1080

AATACCTGAC CGGTTTAACG CCAAATACGA CCTATCGGTT CGGTGGCTAC GCCAAAGTGT   1140

CTGCAGCTGG CCAATCAGTC AGTATTGGTG TCAAAAATTA TGGGGAACT GCGGTCGATG    1200

CGACTATAGG TACGACCAGC TACTCCAATA ATTCGGTAAC TTTTACAACT GGAGCCAATA   1260

ATACTACTGC TACGGTCTAT TTCTATAAAC CCTTGAGCGG TACAGTGTAT GGTGATGATT   1320

TCTATTTGGA AAAATTGTAA AACACCGTAG TTAGAAGAGC AGCGGTTTAG TTCAACCGCT   1380

GCTCTTTTAG CAATACTGCG TGATGACG                                     1408
```

(2) INFORMATION FOR SEQ ID NO:2:

(i) SEQUENCE CHARACTERISTICS:
        (A) LENGTH: 422 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Met Arg Lys Thr Lys Phe Trp Leu Val Leu Ser Leu Ile Ala Thr
 1               5                  10                  15

Ser Leu Ser Ile Phe Ala Cys Lys Lys Asp Ser Ala Thr Lys
                20                  25                  30

Asn Pro Ile Pro Glu Val Ser Lys Ala Lys Ser Thr Lys Leu
                35                  40                  45

Leu Asn Ala Thr Thr Val Ala Thr Thr Asp Tyr Glu Leu Ile Trp
                50                  55                  60

Ser Asp Glu Phe Asn Ser Ser Gly Gly Phe Asp Ser Thr Lys Trp
                65                  70                  75

Ser Tyr Ala Asp Arg Gly Thr Val Ala Trp Asn Lys Tyr Met Thr
                80                  85                  90

Ser Gln Asp Gly Ser Asn Leu Val Leu Arg Met Asp Asn Ala Val
```

```
                    95                  100                 105
Ala Gly Asp Pro Val Ala Tyr His Ala Gly Val Lys Ser Met
                110                 115                 120
Lys Phe Ser Met Thr Tyr Gly Val Glu Val Arg Ala Lys Phe
                125                 130                 135
Thr Gly Val Ser Leu Pro Ala Tyr Ala Gln Gly Arg Gly Ser Trp
                140                 145                 150
Pro Ala Ile Trp Met Met Pro Glu Pro Ala Thr Ala Tyr Gly Gly
                155                 160                 165
Trp Pro Ser Cys Gly Glu Ile Asp Ser Met Glu His Val Asn Asn
                170                 175                 180
Glu Ser Val Met Tyr His Thr Ile His Asn Gly Ser Val Thr Asn
                185                 190                 195
Ala Asn Gly Gly Ser Thr Ala Ser Lys Ser Ala Thr Tyr Asn Thr
                200                 205                 210
Thr Asp Tyr Asn Leu Tyr Thr Met Ile Trp Ser Pro Asn Asp Ile
                215                 220                 225
Arg Phe Tyr Val Asn Asn Ser Leu Gln Tyr Thr Tyr Ala Arg Val
                230                 235                 240
Ser Gly Gly Gly Thr Gln Gln Trp Pro Phe Asp Val Pro Phe Tyr
                245                 250                 255
Leu Ile Leu Asn Gln Ala Gly Gly Ala Gly Trp Pro Gly Ala Ile
                260                 265                 270
Thr Asn Ala Asp Leu Pro Phe Ser Met Gln Val Asp Tyr Val Arg
                275                 280                 285
Val Tyr Lys Leu Pro Leu Phe Ser Asn Gly Asp Phe Glu Ser Gly
                290                 295                 300
Val Ile Tyr Pro Trp Thr Thr Trp Gly Gly Ser Ser Val Val
                305                 310                 315
Ser Thr Asp Ala Arg Thr Gly Thr Lys Cys Ile Arg Glu Thr Gly
                320                 325                 330
Gly Glu Thr Ser Ile Glu Gln Tyr Leu Thr Gly Leu Thr Pro Asn
                335                 340                 345
Thr Thr Tyr Arg Phe Gly Gly Tyr Ala Lys Val Ser Ala Ala Gly
                350                 355                 360
Gln Ser Val Ser Ile Gly Val Lys Asn Tyr Gly Gly Thr Ala Val
                365                 370                 375
Asp Ala Thr Ile Gly Thr Thr Ser Tyr Ser Asn Asn Ser Val Thr
                380                 385                 390
Phe Thr Thr Gly Ala Asn Asn Thr Thr Ala Thr Val Tyr Phe Tyr
                395                 400                 405
Lys Pro Leu Ser Gly Thr Val Tyr Gly Asp Asp Phe Tyr Leu Glu
                410                 415                 420
Lys Leu (2) INFORMATION FOR SEQ ID NO:3:

(i) SEQUENCE CHARACTERISTICS:
        (A) LENGTH: 321 amino acids
        (B) TYPE: amino acid
        (C) STRANDEDNESS:
        (D) TOPOLOGY: linear (ii) MOLECULE TYPE: peptide (iii) HYPOTHETICAL: NO
```

-continued (iv) ANTI-SENSE: NO (v) FRAGMENT TYPE:

(vi) ORIGINAL SOURCE:
    (A) ORGANISM: e13b, Bacillus circulars (xi) SEQUENCE DESCRIPTION: SEQ ID NO:3:

```
Phe Gln Pro Ile Gln Glu Asn Met Gln Ile Arg Ile Gly Tyr Pro Leu
 1               5                  10                  15

Asn Gly Gln Ala Gly Gly Asn Ile Gly Asn Asn Phe Val Asn Tyr Thr
            20                  25                  30

Phe Ile Gly Asn Pro Asn Ala Pro Arg Pro Asp Val Ser Asp Gln Glu
        35                  40                  45

Asp Ile Ser Ile Gly Thr Pro Thr Asp Pro Ala Ile Ala Gly Met Asn
 50                  55                  60

Leu Ile Trp Gln Asp Glu Phe Asn Glu Thr Thr Leu Asp Thr Ser Lys
 65                  70                  75                  80

Trp Asn Tyr Phe Thr Gly Tyr Tyr Leu Asn Asn Asp Pro Ala Thr Trp
                85                  90                  95

Gly Trp Gly Asn Ala Glu Leu Gln His Tyr Thr Asn Ser Thr Gln Asn
            100                 105                 110

Val Tyr Val Gln Asp Gly Lys Leu Asn Ile Lys Ala Met Asn Asp Ser
        115                 120                 125

Lys Ser Pro Gln Asp Pro Asn Arg Tyr Ala Gln Tyr Ser Ser Gly Lys
130                 135                 140

Ile Asn Thr Lys Asp Lys Leu Ser Leu Lys Tyr Gly Arg Val Asp Phe
145                 150                 155                 160

Arg Ala Lys Leu Pro Thr Gly Asp Gly Val Trp Pro Ala Leu Trp Met
                165                 170                 175

Leu Pro Lys Asp Ser Val Tyr Gly Thr Trp Ala Ala Ser Gly Glu Ile
                180                 185                 190

Asp Val Met Glu Ala Arg Gly Arg Leu Pro Gly Ser Val Ser Gly Thr
                195                 200                 205

Ile His Phe Gly Gly Gln Trp Pro Val Asn Gln Ser Ser Gly Gly Asp
210                 215                 220

Tyr His Phe Pro Glu Gly Gln Thr Phe Ala Asn Asp Tyr His Val Tyr
225                 230                 235                 240

Ser Val Val Trp Glu Glu Asp Asn Ile Lys Trp Tyr Val Asp Gly Lys
                245                 250                 255

Phe Phe Tyr Lys Val Thr Asn Gln Gln Trp Tyr Ser Thr Ala Ala Pro
                260                 265                 270

Asn Asn Pro Asn Ala Pro Phe Asp Glu Pro Phe Tyr Leu Ile Met Asn
                275                 280                 285

Leu Ala Val Gly Gly Asn Phe Asp Gly Gly Arg Thr Pro Asn Ala Ser
290                 295                 300

Asp Ile Pro Ala Thr Met Gln Val Asp Tyr Val Arg Val Tyr Lys Phe
305                 310                 315                 320

Gln
```

(2) INFORMATION FOR SEQ ID NO:4:

(i) SEQUENCE CHARACTERISTICS:
        (A) LENGTH: 276 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE:

(vi) ORIGINAL SOURCE:
  (A) ORGANISM: gub, Rhodothermus marinus (xi) SEQUENCE DESCRIPTION: SEQ ID NO:4:

```
Lys Met Met Arg Arg Thr Ala Phe Leu Leu Ser Val Leu Ile Gly Cys
 1               5                  10                  15

Ser Met Leu Gly Ser Asp Arg Ser Asp Lys Ala Pro His Trp Glu Leu
            20                  25                  30

Val Trp Ser Asp Glu Phe Asp Tyr Ser Gly Leu Pro Asp Pro Glu Lys
            35                  40                  45

Trp Asp Tyr Asp Val Gly Gly His Gly Trp Gly Asn Gln Glu Leu Gln
 50                  55                  60

Tyr Tyr Thr Arg Ala Arg Ile Glu Asn Ala Arg Val Gly Gly Gly Val
 65              70                  75                  80

Leu Ile Ile Glu Ala Arg His Glu Pro Tyr Glu Gly Arg Glu Tyr Thr
                85                  90                  95

Ser Ala Arg Leu Val Thr Arg Gly Lys Ala Ser Trp Thr Tyr Gly Arg
            100                 105                 110

Phe Glu Ile Arg Ala Arg Leu Pro Ser Gly Arg Gly Thr Trp Pro Ala
            115                 120                 125

Ile Trp Met Leu Pro Asp Arg Gln Thr Tyr Gly Ser Ala Tyr Trp Pro
130                 135                 140

Asp Asn Gly Glu Ile Asp Ile Met Glu His Val Gly Phe Asn Pro Asp
145                 150                 155                 160

Val Val His Gly Thr Val His Thr Lys Ala Tyr Asn His Leu Leu Gly
                165                 170                 175

Thr Gln Arg Gly Gly Ser Ile Arg Val Pro Thr Ala Arg Thr Asp Phe
            180                 185                 190

His Val Tyr Ala Ile Glu Trp Thr Pro Glu Glu Ile Arg Trp Phe Val
            195                 200                 205

Asp Asp Ser Leu Tyr Tyr Arg Phe Pro Asn Glu Arg Leu Thr Asp Pro
210                 215                 220

Glu Ala Asp Trp Arg His Trp Pro Phe Asp Gln Pro Phe His Leu Ile
225                 230                 235                 240

Met Asn Ile Ala Val Gly Gly Ala Trp Gly Gly Gln Gln Gly Val Asp
                245                 250                 255

Pro Glu Ala Phe Pro Ala Gln Leu Val Val Asp Tyr Val Arg Val Tyr
            260                 265                 270

Arg Trp Val Glu
            275
```

(2) INFORMATION FOR SEQ ID NO:5:

(i) SEQUENCE CHARACTERISTICS:
    (A) LENGTH: 285 amino acids
    (B) TYPE: amino acid
    (C) STRANDEDNESS:
    (D) TOPOLOGY: linear (ii) MOLECULE TYPE: peptide (iii) HYPOTHETICAL: NO (iv) ANTI-SENSE: NO (v) FRAGMENT TYPE:

(vi) ORIGINAL SOURCE:
(A) ORGANISM: Flavobacterium Keratolyticus (xi) SEQUENCE DESCRIPTION: SEQ ID NO:5:

```
Lys Ala Lys Ala Ser Thr Lys Leu Leu Asn Ala Thr Thr Val Ala Thr
 1               5                  10                  15

Thr Asp Tyr Glu Leu Ile Trp Ser Asp Glu Phe Asn Ser Ser Gly Gly
            20                  25                  30

Phe Asp Ser Thr Lys Trp Ser Tyr Ala Asp Arg Gly Thr Val Ala Trp
             35                  40                  45

Asn Lys Tyr Met Thr Ser Leu Pro Ala Tyr Ala Ser Gln Asp Gly Ser
 50                  55                  60

Asn Leu Val Leu Arg Met Asp Asn Ala Val Ala Gly Asp Pro Val
 65                  70                  75                  80

Ala Tyr His Ala Gly Gly Val Lys Ser Met Gly Lys Phe Ser Met Thr
                 85                  90                  95

Tyr Gly Lys Val Glu Val Arg Ala Lys Phe Thr Gln Gly Arg Gly Ser
                100                 105                 110

Trp Pro Ala Ile Trp Met Met Pro Glu Pro Ala Thr Ala Tyr Gly Gly
                115                 120                 125

Trp Pro Ser Cys Gly Glu Ile Asp Ser Met Glu His Val Asn Asn Glu
130                 135                 140

Ser Val Met Tyr His Thr Ile His Asn Gly Ser Val Thr Asn Ala Asn
145                 150                 155                 160

Gly Gly Ser Thr Ala Ser Lys Ser Ala Thr Tyr Asn Thr Thr Asp Tyr
                165                 170                 175

Asn Leu Tyr Thr Met Ile Trp Ser Pro Asn Asp Ile Arg Phe Tyr Val
                180                 185                 190

Asn Asn Ser Leu Gln Tyr Thr Tyr Ala Arg Val Ser Gly Gly Gly Thr
                195                 200                 205

Gln Gln Trp Pro Phe Asp Val Pro Phe Tyr Leu Ile Leu Asn Gln Ala
                210                 215                 220

Gly Gly Ala Gly Trp Pro Gly Ala Ile Thr Asn Ala Asp Leu Pro Phe
225                 230                 235                 240

Ser Met Gln Val Asp Tyr Val Arg Val Tyr Lys Leu Pro Leu Phe Ser
                245                 250                 255

Asn Gly Asp Phe Glu Ser Gly Val Ile Tyr Pro Trp Thr Thr Trp Gly
                260                 265                 270

Gly Gly Ser Ser Val Val Ser Thr Asp Ala Arg Thr Gly
                275                 280                 285
```

(2) INFORMATION FOR SEQ ID NO:6:

(i) SEQUENCE CHARACTERISTICS:
(A) LENGTH: 26 bases
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(ix) FEATURE:
            (D) OTHER INFORMATION: N=INOSINE (i)

(xi) SEQUENCE DESCRIPTION: SEQ ID NO:6:

AACGCNACNA CNGTNGCNAC NACNGA                                            26

(2) INFORMATION FOR SEQ ID NO:7:

(i) SEQUENCE CHARACTERISTICS:
            (A) LENGTH: 26 bases
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(ix) FEATURE:
            (D) OTHER INFORMATION:; N=INOSINE (i)

(xi) SEQUENCE DESCRIPTION: SEQ ID NO:7:

AATGCNACNA CNGTNGCNAC NACNGA                                            26

(2) INFORMATION FOR SEQ ID NO:8:

(i) SEQUENCE CHARACTERISTICS:
            (A) LENGTH: 19 bases
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

TTGAATTCGT CNGACTCCA                                                    19

(2) INFORMATION FOR SEQ ID NO:9:

(i) SEQUENCE CHARACTERISTICS:
            (A) LENGTH: 19 bases
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

TTAAACTCAT CNGACTCCA                                                    19

(2) INFORMATION FOR SEQ ID NO:10:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

ATGGACAACG CNGTNGT                                17

(2) INFORMATION FOR SEQ ID NO:11:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

ATGGATAATG CNGTNGT                                17

(2) INFORMATION FOR SEQ ID NO:12:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(ix) FEATURE:
        (D) OTHER INFORMATION: N= INOSINE (i)

(xi) SEQUENCE DESCRIPTION: SEQ ID NO:12:

GTNGACTTTT NACNCCNCCN GCGTGGTA                    28

(2) INFORMATION FOR SEQ ID NO:13:

(i) SEQUENCE CHARACTERISTICS:
        (A) LENGTH: 28 bases
        (B) TYPE: nucleic acid
        (C) STRANDEDNESS: single

```
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(ix) FEATURE:
          (D) OTHER INFORMATION: N=INOSINE (i)

(xi) SEQUENCE DESCRIPTION: SEQ ID NO:13:

GTNGACTCTT NACNCCNCCN GCTTGGTA                                               28
```

ENDO-β-GALACTOSIDASE

This invention was made, at least in part, with government support under Grant No. N00014-93-1-0466 from the Office of Naval Research and Development Command, such that the United States Government may have certain rights herein.

1. INTRODUCTION

The present invention relates to purified and isolated nucleic acid encoding the endo-β-galactosidase from *Flavobacterium keratolyticus* (referred to herein as "ENDO-A"), and to purified ENDO-A protein. The endo-β-galactosidase of the invention may be used in a process which enzymatically de-antigenizes human erythrocytes bearing the $A_1$ antigen. The resulting erythrocytes may be transfused into individuals who would be otherwise unable to safely tolerate a transfusion of type $A_1$ blood.

2. BACKGROUND OF THE INVENTION

2.1 ENZYMATIC CONVERSION OF BLOOD TYPE

Based on the presence or absence of defined antigens, human blood may be classified into four main types, or groups, designated O, A, B, and AB. There are three major recognized subtypes of blood type A, known as $A_1$, $A_{int}$, and $A_2$.

The carbohydrate structures associated with $A_1$, $A_2$, B and O blood types are shown in FIGS. 1A–1D. While $A_2$ and B antigens consist of a single, external, antigenic component, the $A_1$ antigen comprises two antigenic components, the major component having an external residue (FIG. 1A) and the minor component having both an external as well as an internal residue (FIG. 1A), relative to the carbohydrate chain.

Individuals with type A red cells have, in their plasma, antibodies directed against type B red cells (anti-B antibodies). Conversely, individuals with type B red cells have anti-A antibodies in their plasma. Persons with type O blood have antibodies directed toward both A and B antigens.

The presence of such antibodies makes blood transfusions problematic. If the host to a transfusion carries antibodies against the donor blood, a severe and potentially life-threatening reaction can result. The only blood type that can be safely transfused into persons of all blood types is type O blood, which is often referred to as "universal donor" blood. However, the availability of type O blood is insufficient to meet transfusion needs, because less than half of the population has type O blood.

Moreover, as a result of the limited shelf-life of donated blood, a disparity between the supply of blood available and transfusion needs often leads to the destruction of large quantities of blood stored in blood banks internationally.

In order to satisfy the demand for safely transfusable blood, and to more efficiently utilize the donated blood supply, technology has been developed which converts erythrocytes which are type A, B, or AB to "universal donor" blood.

Figure 1C:
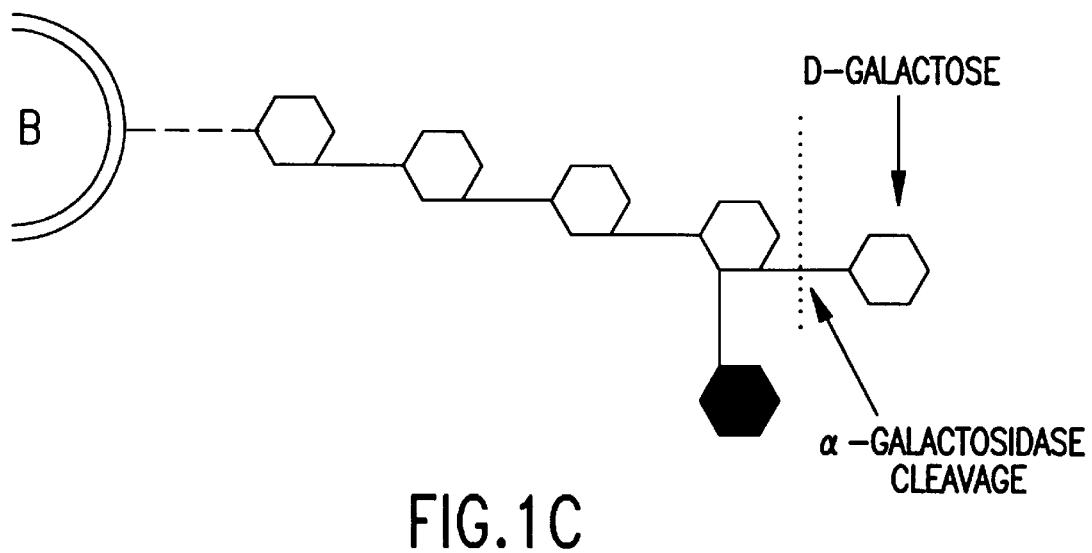
Figure 1D:
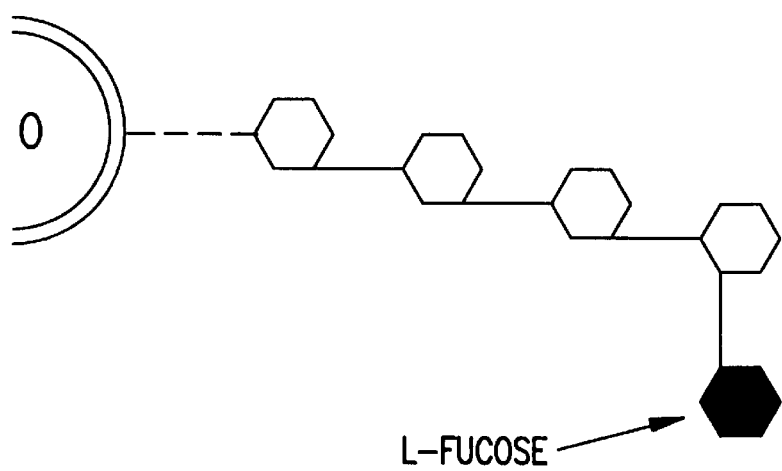

Conversion of blood type B to type O may be accomplished using α-galactosidase enzyme originating from green coffee bean ("B-zyme"), which cleaves at the α1,3 bond linking the terminal galactose to a carbohydrate structure identical to the H-antigen associated with type O blood (cleavage indicated by a dotted line in FIG. 1C). Blood converted by this method has been safely transfused into patients (see, for example, U.S. Pat. Nos. 4,330,619 and 4,427,777; Lenny et al., 1991, Blood 77:1383–1388; Goldstein, 1989, Transfusion Medicine Reviews III(3):206–212). The coffee bean α-galactosidase gene has been cloned, characterized, and expressed to produce recombinant enzyme for use in the conversion of type B erythrocytes (Zhu and Goldstein, 1994, Gene 140:227–231).

Likewise, type $A_{int}$-$A_2$ blood has been successfully deantigenized using α-N-acetyl-galactosaminidase enzyme originating in chicken liver ("A-zyme"; U.S. Pat. No. 4,609,627; Goldstein et al., 1984, "Enzymatic Removal of Group A Antigens" in *Abstracts of the 18th Congress of the ISBT*, Karger, Munich, p. 86; Goldstein, 1989, Transfusion Medicine Reviews III(3):206–212). The chicken liver α-N-acetylgalactosaminidase gene has been cloned, characterized, and expressed (Zhu and Goldstein, 1993, Gene 137:309–314).

Because the $A_1$ antigen comprises an internal as well as an external antigenic component, even after treatment with α-N-acetylgalactosaminidase, internal antigen remains. An endo-β-galactosidase is required to remove the internal antigen. Prior to the present invention, however, an enzyme having the specificity, efficiency, and purity necessary for conversion of type $A_1$ erythrocytes, on a scale commensurate with transfusion requirements in the United States and internationally, has been unavailable.

2.2 ENDO-β-GALACTOSIDASES

As reviewed in Fukuda, 1995, "Preparation and Analysis of Glycoconjugates", in *Current Protocols in Molecular Biology*, Supplement 32, John Wiley & Sons, §§ 17.17.6–17.17.13, endo-β-galactosidases were discovered during a search for a keratan sulfate-degrading enzyme (Id., citing Hirano and Meyer, 1971, Biochem. Biophys. Res. Commun. 44:1371–1375; Nakasawa and Suzuki, 1975, J. Biol. Chem. 250:912–917; Kitamikado et al., 1970, Bull. Jap. Soc. Sci. Fish. 36:592–596; Kitamikado et al., 1970, Bull. Jap. Soc. Sci. Fish. 36:1172–1174; Kitamikado et al., 1970, Bull. Jap. Soc. Sci. Fish. 36:1175–1180).

A keratan-sulfate degrading endo-β-galactosidase from *Flavobacterium keratolyticus* was identified by Kitamikado (1981, J. Biological Chem. 256:3906–3909), and purified to a specific activity substantially less than that achieved in the present invention. Amano et al. (1991, J. Biological Chem. 266:11461–11477) reports that the endo-β-galactosidase from *Flavobacterium keratolyticus* has a wide substrate specificity, among which are ABO blood group determinants. Endo-β-galactosidases from *Escherichia freundii* (Fukuda, 1981, J. Biol. Chem. 256:3900–3905) and *Bacteroides fragilis* (Scudder et al., 1983, Biochem. J. 213:485–494) have also been characterized.

3. SUMMARY OF THE INVENTION

The present invention relates to purified and isolated nucleic acid encoding the endo-β-galactosidase from *Flavobacterium keratolyticus* (referred to herein as "ENDO-A"), and to purified ENDO-A protein. It is based, at least in part, on the purification of ENDO-A protein to a degree of purity and specific activity greater than has hitherto been known in the art, and on the cloning and characterization of nucleic acid encoding ENDO-A. The endo-β-galactosidase of the invention, "ENDO-A", may be used, in conjunction with α-N-acetylgalactosaminidase, to enzymatically de-antigenize human erythrocytes bearing the $A_1$ antigen.

The resulting erythrocytes may be transfused into individuals who would be otherwise unable to tolerate a transfusion of type $A_1$ blood. In alternative embodiments, the ENDO-A of the invention may be used to degrade keratan sulfate (for example, in the food industry), or in blood typing reactions.

4. DESCRIPTION OF THE DRAWINGS

FIGS. 1A–D. Schematic diagrams of antigen structures associated with blood type: (A) the minor component of $A_1$ antigen, containing both internal as well as external antigenic residues; (B) the major component of $A_1$ antigen, containing an external antigenic residue; (C) the antigen associated with type B blood and (D) the carbohydrate structure associated with universal donor type O blood.

FIG. 2. Nucleic acid and amino acid sequences for *F. keratolyticus* ENDO-A (SEQ ID NO:1, SEQ ID NO:2). The oligomers, designated ED series, which were used in the cloning and sequencing, are shown under the nucleotide sequence with arrows indicating 5' to 3' direction. Asterisks (*) next to the oligomers ED-1* through ED-4* indicate the degenerate nature of these sequences, while all others (ED-5 through ED-12) have exact sequences as underlined. The first 46 amino acid residues may constitute a putative signal peptide which is cleaved during biosynthesis.

Figure 3:
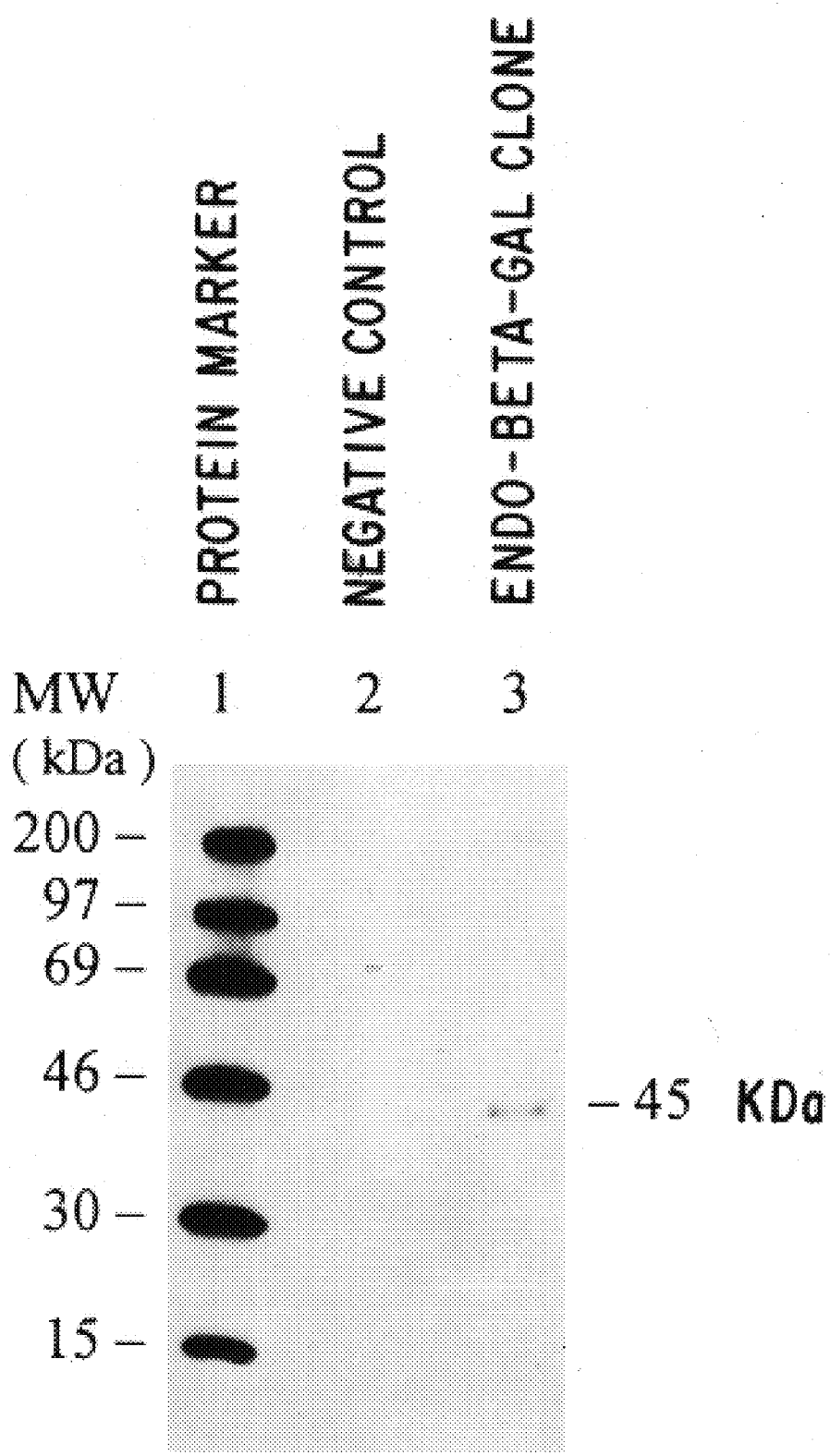

FIG. 3. Autoradiogram of $^{35}$S methionine labeled protein produced in a reticulocyte lysate transcription translation system. The negative control was minus the DNA encoding ENDO-A. The product of the ENDO-A clone was immunoprecipitated and subjected to SDS-PAGE.

FIG. 4. Alignments for maximal amino acid homology between *F. keratolyticus* ENDO-A and bacterial endo-β-glucanases. E13b (SEQ ID NO:3) and gub (SEQ ID NO:4) represent *Bacillus circulans* glucan endo-1,3-b-glucosidase and *Rhodothermus marinus* endo-β-1.3-1.4-glucanase, respectively. Endo-gal (SEQ ID NO:5) in the figure is ENDO-A, wherein the beginning of the sequence, KAKA..., corresponds to residue 38 in FIG. 2. Only partial sequences of these three enzymes are shown, with numbers indicating the positions of amino acid residues. The gaps within the sequences are introduced in order to show the highly homologous regions, which are boxed.

Figure 5:
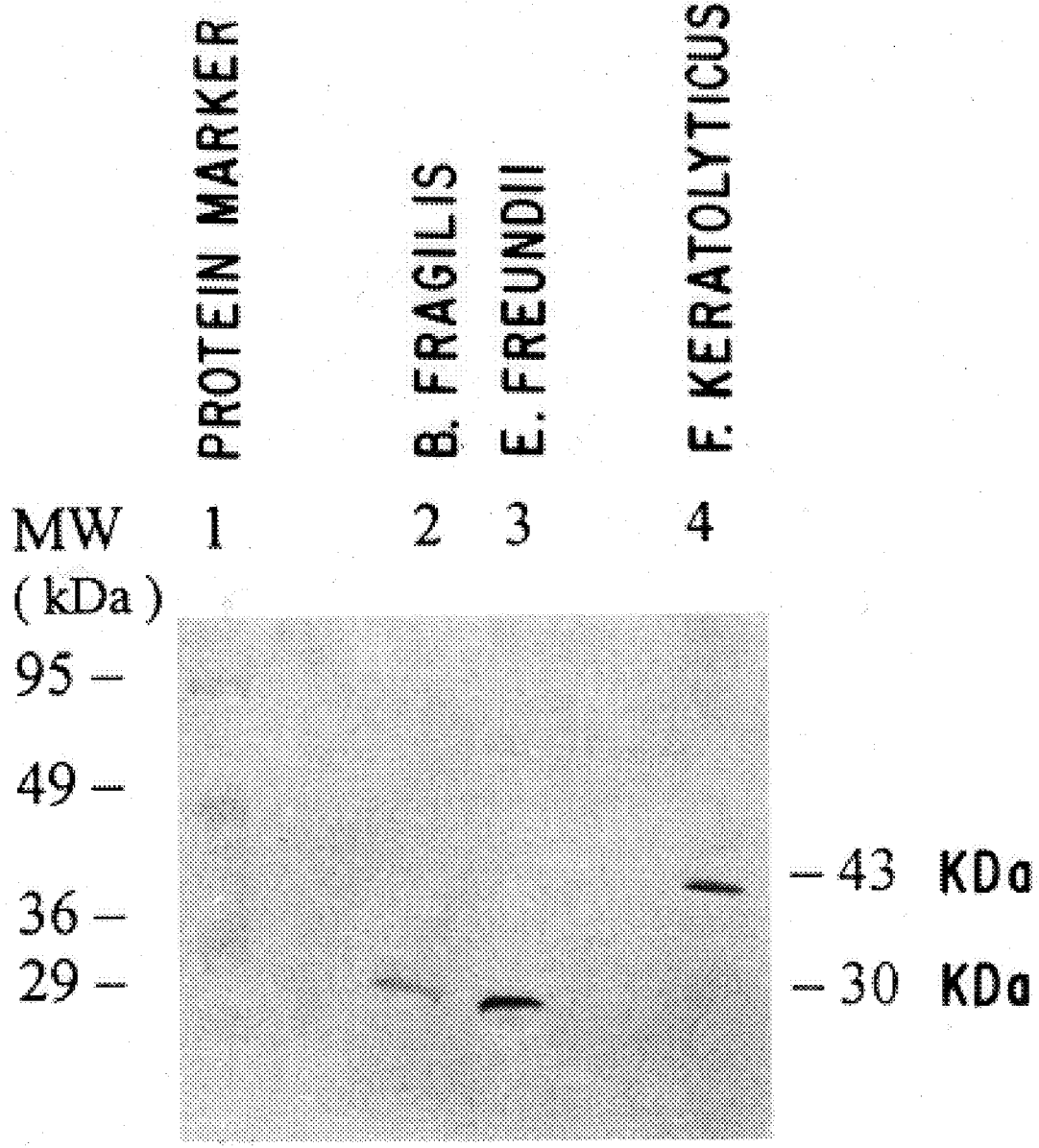

FIG. 5. Endo-β-galactosidase preparations from *F. keratolyticus, B. fragilis* and *E. freundii* were subjected to SDS-PAGE and then transferred to a nitrocellulose membrane and a Western blot was carried out using rabbit anti-serum raised against endo-β-galactosidase from *B. fragilis*.

Figure 6:
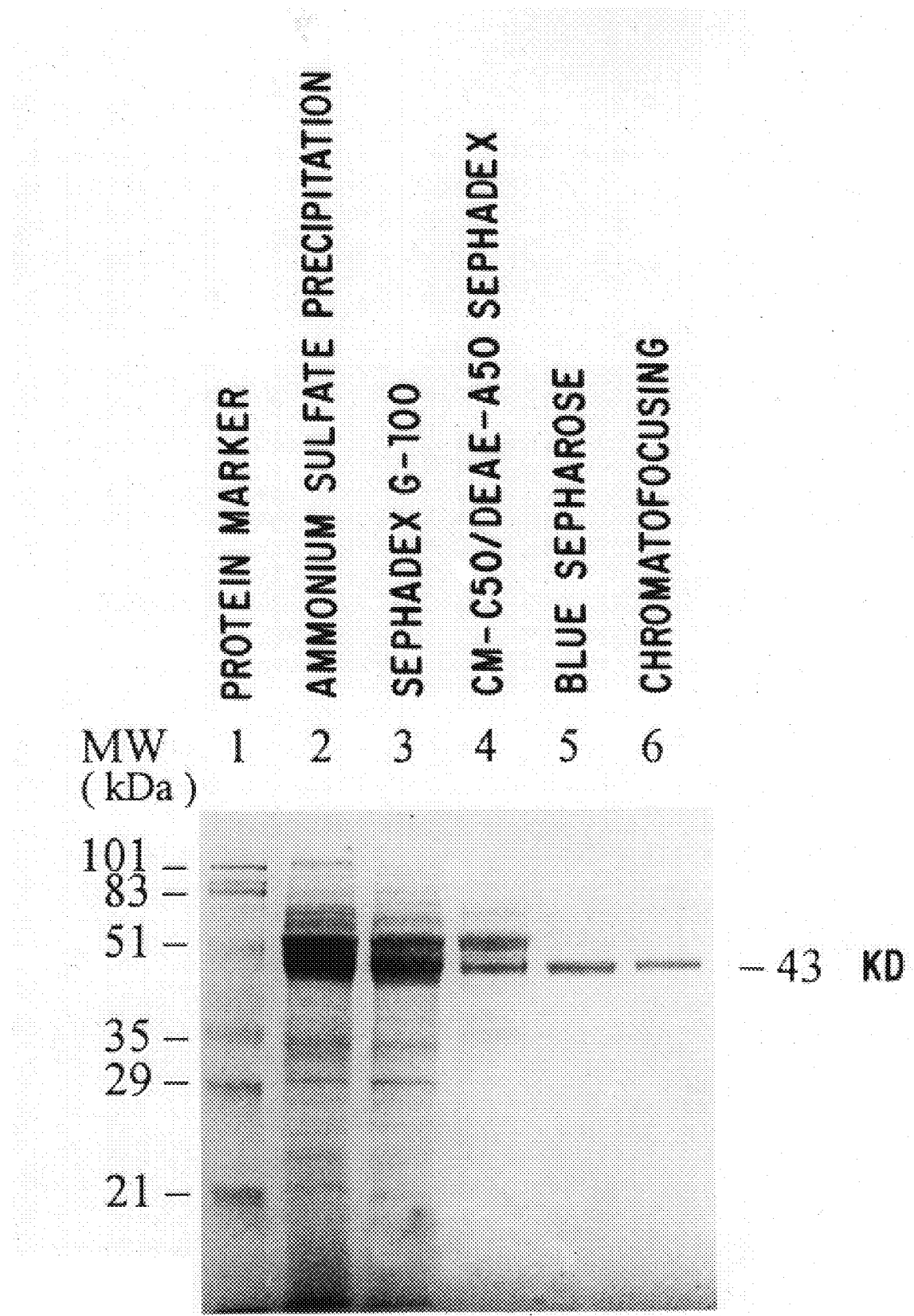

FIG. 6. SDS-PAGE analysis of ENDO-A purification. Samples from each step of the enzyme purification were analyzed by SDS-PAGE stained with Coomassie blue. Lane 1, protein markers; Lane 2, $(NH4)_2 SO_4$ precipitation; Lane 3, Sephadex G-100; Lane 4, CM/DEAE Sephadex; Lane 5, blue Sephadex and Lane 6, chromatofocusing.

Figure 7:
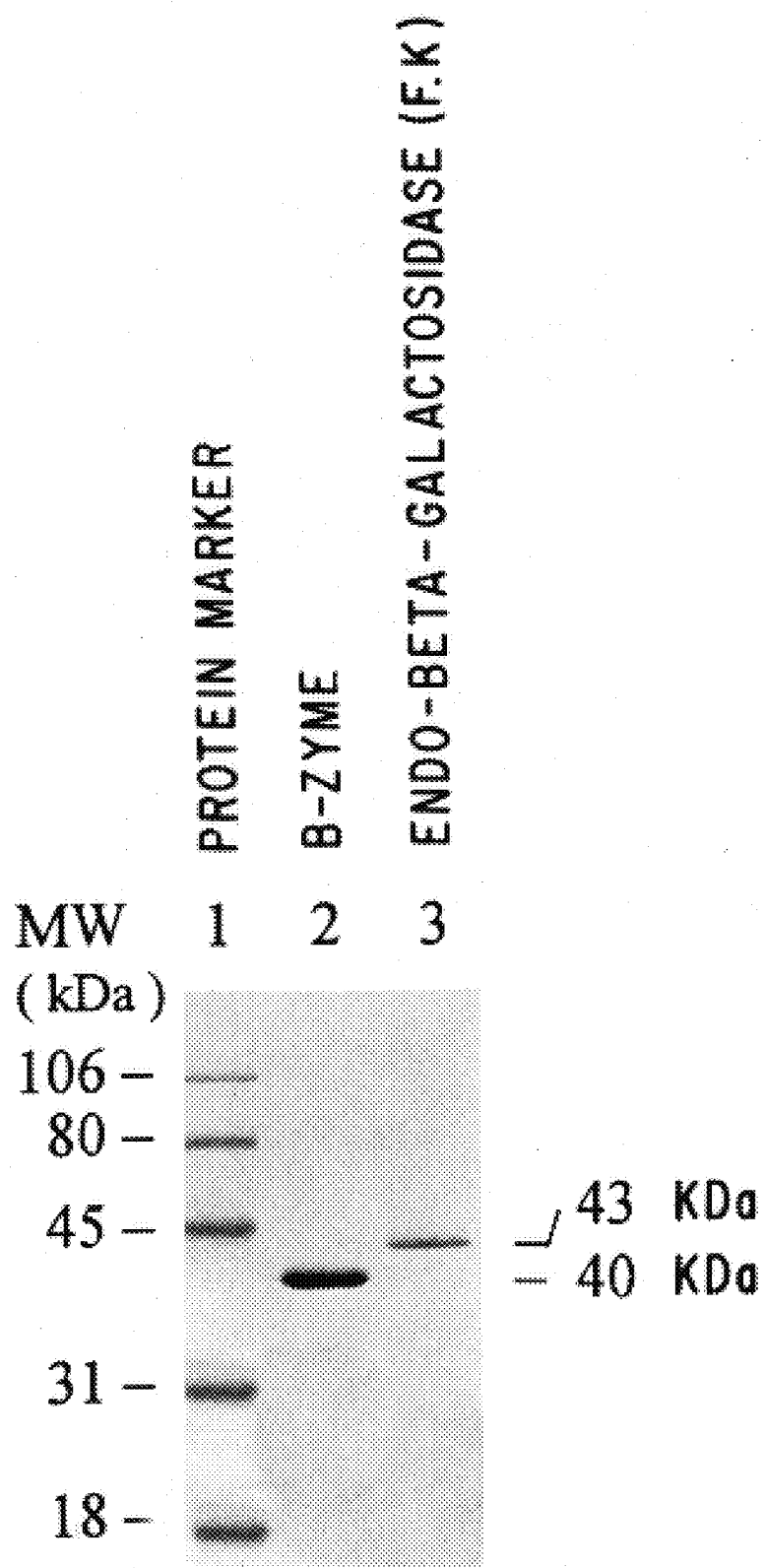

FIG. 7. SDS-PAGE characterization of the molecular weight of ENDO-A. Lane 1 Molecular weight markers, Lane 2 coffee bean α-galactosidase (B-zyme), Lane 3 ENDO-A.

Figure 8:
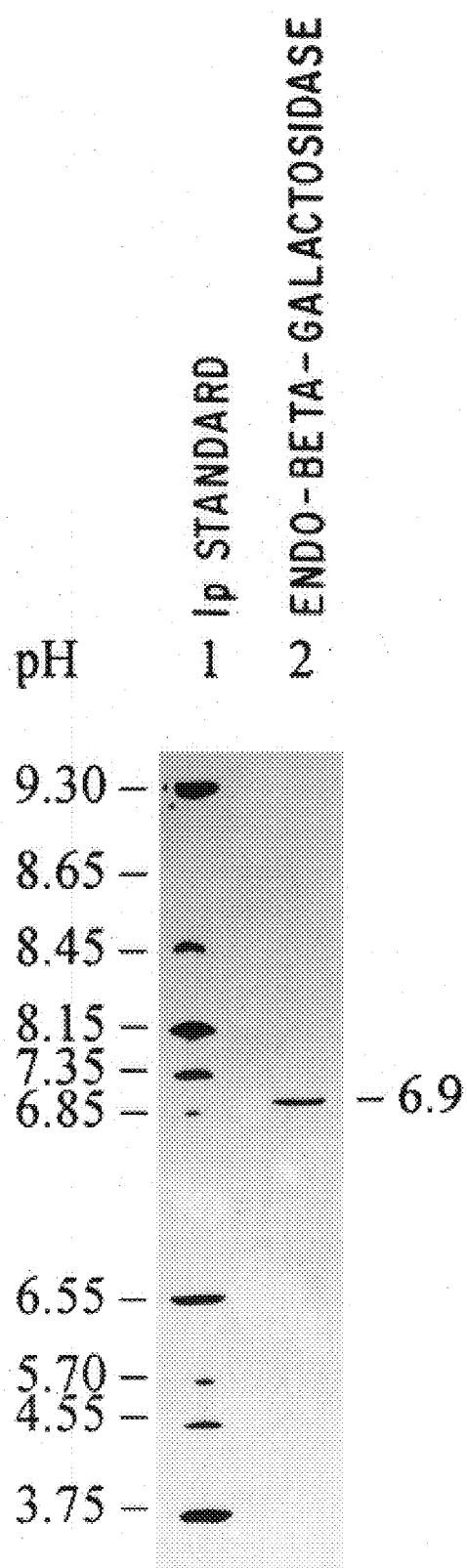

FIG. 8. Determinations of isoelectric point of ENDO-A by isoelectric focusing. Lane 1 is a mixture of protein standards with corresponding pI values shown on the left of the figure. Lane 2 is purified ENDO-A.

5. DETAILED DESCRIPTION OF THE INVENTION

The present invention relates to nucleic acid molecules encoding ENDO-A, ENDO-A proteins, peptide fragments and derivatives, and antibodies directed toward ENDO-A. In addition, the invention relates to pharmacological compositions comprising ENDO-A protein.

The ENDO-A of the invention may be used to cleave antigenic residues from cells bearing the internal antigen depicted in FIG. 1A. In one specific, nonlimiting embodiment of the invention, ENDO-A may be used in conjunction with chicken liver N-acetylgalactosaminidase to remove antigenic structures associated with the $A_1$ blood type.

5.1. ENDO-A-ENCODING NUCLEIC ACIDS

The present invention relates to purified and isolated nucleic acid molecules encoding ENDO-A. It is based, at least in part, on the cloning and characterization of ENDO-A-encoding nucleic acid from the bacterium, *Flavobacterium keratolyticus*.

In one nonlimiting embodiment, the present invention provides for a purified and isolated nucleic acid encoding ENDO-A. For example, and not by way of limitation, the invention provides for a nucleic acid molecule having a sequence as set forth in FIG. 2 (SEQ ID NO:1), as comprised in the deposited plasmid pCR-ED. The present invention also provides for nucleic acid molecules which are at least 90 percent (and preferably at least 95 percent) homologous to the ENDO-A sequence set forth in FIG. 2 (SEQ ID No:1), wherein the percent homology is defined as the percentage of identical nucleic acids occurring in molecules which have been aligned in a manner which pairs residues, for comparison, with the greatest degree of similarity (e.g., MacVector, Version 4.1, "Sequence Analysis Software for the MacIntosh", International Biotechnologies, Inc., a subsidiary of Eastman Kodak Co., New Haven, Conn.). In still further nonlimiting embodiments, the present invention provides for a nucleic acid molecule, at least 30 and preferably at least 50 nucleotides in length, which hybridizes with a nucleic acid molecule having a sequence as set forth for ENDO-A in FIG. 2 (SEQ ID NO:1), or as contained in plasmid pCR-ED under stringent conditions, wherein stringent conditions are defined as hybridization in 50 percent formamide at 42° C., followed by washing in 0.1xSSC and 0.1 percent sodium dodecyl sulfate at 68° C. The nucleic acids of the invention may be DNA (including cDNA) or RNA.

The present invention also provides for purified and isolated nucleic acid molecules which encode a protein having an amino acid sequence as set forth for ENDO-A in FIG. 2 (SEQ ID NO:2) and to (i) nucleic acid molecules at least 90 percent (and preferably at least 95 percent) homologous and (ii) nucleic acid molecules (at least 30 or at least 50 nucleotides in length) which hybridize under stringent conditions, thereto.

Multiple copies of an ENDO-A encoding nucleic acid may be readily produced by inserting the nucleic acid into an appropriate cloning vector and introducing that vector into a suitable host cell, such as, but not limited to, a bacterial cell.

5.2. EXPRESSION OF ENDO-A

The ENDO-A encoding nucleic acid molecules set forth above may be expressed in a suitable host cell, for example, a microorganism such as a bacterial, yeast (e.g., *Pichia pastoris*), fungal, or algae cell, or a plant, insect, or vertebrate host cell. An ENDO-A encoding nucleic acid molecule may be inserted into a suitable expression vector, including a plasmid, cosmid, phage, or virus vector. The vector may further comprise control elements which aid in the transcription, translation, and/or processing of ENDO-A, as well as one or more selection marker. For example, useful control elements include one or more of the following: a promoter/enhancer element, polyadenylation signal, transcriptional terminator, translational initiation site and terminator, ribosome binding site, nuclear localization signal, and secretory signal sequence. The vector may then be introduced, using standard techniques, into a suitable host cell for expression.

5.3. ENDO-A PROTEINS

The present invention relates to purified and isolated ENDO-A proteins which may be encoded by the nucleic acid molecules described in Section 5.1, above, and expressed using methods described in Section 5.2, above. Alternatively, ENDO-A protein may be prepared from *Flavobacterium keratolyticus* using methods as set forth in Section 6, below. In specific, nonlimiting embodiments, ENDO-A has a molecular weight of approximately 40–45 kD.

In one nonlimiting embodiment, the present invention provides for a purified and isolated ENDO-A protein having an amino acid sequence as set forth in FIG. 2 (SEQ ID NO:2), and/or as encoded by nucleic acid contained in the plasmid pCR-ED.

The present invention also relates to proteins having amino acid sequences which are functionally equivalent to the amino acids sequences set forth in FIG. 2 (SEQ ID NO:2). For example, one or more of the amino acid residues within the sequence may be substituted with another amino acid residue of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also within the scope of the invention are ENDO-A proteins that have been modified by glycosylation, proteolytic cleavage, or incorporation into a larger molecule.

5.4. ANTI-ENDO-A ANTIBODIES

According to the invention, ENDO-A protein, as set forth above, or an immunogenic fragment thereof, may be used as an immunogen to generate anti-ENDO-A antibodies.

To improve the likelihood of producing an anti-ENDO-A immune response, the amino acid sequence of ENDO-A may be analyzed in order to identify portions of the ENDO-A molecule which may be associated with greater immunogenicity. For example, the amino acid sequence may be subjected to computer analysis to identify surface epitopes, according to the method of Hopp and Woods, 1981, Proc. Natl. Acad. Sci. U.S.A. 78:3824–3828. Such epitopes may then be isolated and incorporated into a suitable carrier molecule.

For preparation of monoclonal antibodies toward ENDO-A, any technique which provides for the production of antibody molecules by a continuous cell line or by an organism may be used. For example, and not by way of limitation, the hybridoma technique originally developed by Kohler and Milstein (1975, Nature 256:495–497), or the trioma technique (Kozbor et al., 1983, Immunology Today 4:72), or other techniques used for monoclonal antibody production, including methods for producing chimeric, humanized, or primatized antibodies, may be employed.

Alternatively, polyclonal antibodies directed toward ENDO-A may be prepared by methods known in the art. Various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, and keyhole limpet hemocyanin.

The present invention further provides for nucleic acids encoding immunoglobulin molecules directed toward ENDO-A, including nucleic acids encoding single chain antibodies as well as conventional antibody molecules.

Antibody molecules may be purified by known techniques, such as immunoabsorption or immunoaffinity chromatography, chromatographic methods such as HPLC, or combinations thereof.

The present invention also provides for antibody fragments directed toward ENDO-A, including, but not limited to, F(ab')$_2$ and Fab fragments.

6. EXAMPLE: MOLECULAR CLONING OF THE ENDO-A GENE

6.1. EXPERIMENTAL

6.1.1. MATERIALS

Reagents: G-100 Sephadex, CM-C50 Sephadex, DEAE-A50 Sephadex, Blue-Sepharose cL-6B, nickel column, poly buffer, polybuffer exchanger for chromatofocusing and Ampholine PAGplate for IEF were purchased from Pharmacia LKB Biotechnology. Easy DNA kit and original TA cloning kit were obtained from Invitrogen, PCR in vitro cloning kit was from Takara Shuzo Co., Ltd., Wizard Minipreps, Maxipreps, PCR preps DNA purification systems and TNT T7 coupled reticulocyte lysate in vitro translation system were purchased from Promega. Multi prime DNA labeling systems and $\alpha$ $^{32}$p dCTP were obtained from Amersham. $^{35}$S-methionine (translation grade) was from DuPont. Restriction enzymes were obtained from Boehringer Mannheim and New England Biolabs. Quikhyb™ rapid hybridization solution and sonicated salmon sperm DNA were purchased from Stratagene. Molecular Biology certified agarose was from Bio-Rad, NuScience™ GTG low melting temperature agarose was from FMC.

Culture Medium And Bacterial Growth: The medium for culturing *F. keratolyticus* contains 1% bacto-tryptone (Difco); 0.1% selected yeast extract (Gibco and BRL); 0.2% NaCl. The bacteria grew at 25° C. for 5 days prior to the collection of the culture supernatant.

6.1.2. ISOLATION AND PURIFICATION OF ENDO-A

All purification procedures were performed at 4° C., following the method developed by Kitamikado et al. (1981, J. Biological Chem. 256:3906–3909) with several modifications. Briefly, the culture supernatant was first concentrated by ultrafiltration prior to precipitation with ammonium sulfate at 80% saturation. The dissolved precipate was then subjected to various chromatographic steps as described by Kitamikado et al.(1981, J. Biological Chem. 256:3906–3909) including G-100 Sephadex, a combination of CM-Sephadex C-50 DEAE-Sephadex A-50 and then Blue sepharose-CL6B chromatography. Finally, ENDO-A was purified by chromatofocusing chromatography instead of a second DEAE-sephadex A-50 chromatographic step.

The blue sepharose pool was concentrated and equilibrated with 25 mM Imidazole, pH 6.8 (starting buffer). The enzyme solution was applied to a chromatofocusing column (1 ml of polybuffer exchanger 94) which was equilibrated with starting buffer. The column was washed with starting buffer and eluted with polybuffer 74-HCl, pH 5.0. The unabsorbed fractions contained all of the ENDO-A activity.

6.1.3. CHARACTERIZATION OF PURIFIED ENDO-A

ENDO-A Activity: ENDO-A activity was assayed by using keratan sulfate isolated from bovine cornea (Sigma) according to the method set forth in Scudder et al., 1983, Biochem. J. 213: 485–495. The reaction mixture contained 100 mg of keratan sulfate and an appropriate amount of the enzyme (10 ml enzyme dilution), pH 5.8 in 50 ml of 50 mM sodium acetate buffer containing 10 mg BSA, pH 5.8. After incubation at 37° C. for 10 minutes, 500 ml of carbonate cyanide solution was added to stop the reaction, followed by 500 ml of the ferricyanide solution. After mixing, the tubes were capped with glass bulbs and heated in a boiling water bath for 15 minutes. The tubes were then cooled in a water bath, 2.5 ml of the ferric iron solution was added, and the samples were mixed. A blue color developed which was spectrophotometrically measured after 15 minutes at 690 nm. Separate standards for the various monosaccharides were analyzed in view of the differences in their reducing power. One unit of the enzyme was defined as the amount of enzyme required to release 1 mmol of reducing galactose per minute at 37° C. The specific activity of the enzyme was expressed as units per mg of protein. Protein was determined by the BCA method (Pierce) using BSA as the standard.

Electrophoresis and Immunoblotting: Following SDS/PAGE, the protein samples were immunoblotted using antibody raised against endo-β-galactosidase from *B. fragilis* (1:200) and anti-rabbit IgG (T-C) conjugated with alkaline phosphatase (1:7500, Promega). Blots were developed using BLIP/NBT (Kirkegaard & Perry Laboratories).

Isoelectric focusing (IEF): Isoelectricfocusing was performed using the multiphor system (Pharmacia Biotech). The IEF gel contained 5.25% polyacrylamide, 6M urea and ampholine. The pH gradient was formed with 1M $H_3PO_4$ at the acid end and 1M NaOH at the base end. After loading, a sample gel was run at 500 V for 30 min., then the voltage was increased to 1200V and run for 3 hours. When the current dropped to 4 mA, the run was stopped. The gel was stained with 0.15% Coomassie blue, 45% methanol, and 10% acetic acid, and then was de-stained with 25% methanol and 10% acetic acid.

6.1.4. PEPTIDE SEQUENCING AND OLIGONUCLEOTIDE DESIGN

N-terminal peptide sequencing: Purified ENDO-A was subjected to SDS-PAGE and electroblotted onto Problott™ membrane (Applied Biosystems). The membrane was then stained with 0.1% Coomassie Blue R-250 in 40% methanol/1% acetic acid and destained with 50% methanol. A 43kd protein band was excised and analyzed by an ABI 477A/120A amino acid sequencer.

Internal peptide sequencing: Purified ENDO-A (4 nmol) was treated with 2 mg of CNBr in 70% of formic acid. The reaction was incubated at room temperature for 24 hours, in the dark, with occasional agitation. CNBr-cleaved peptides were separated by reverse phase HPLC and further purified by C4 reverse phase HPLC if necessary, prior to peptide sequencing.

Based on the N-terminal sequence of purified ENDO-A (pep-1 in FIG. 5), two oligomers were designed, namely ED-1*, 5'-AAC/T-GCI-ACI-ACI-GTI-GCI-ACI-ACI-GA-3' (SEQ ID NO:6 and SEQ ID NO:7), and ED-2*, 5'-TT G/A-AAT/C-TCG/A-TCN-GA(CT)C-CA-3' (SEQ ID NO:8 and SEQ ID NO:9). Similarly, based on an internal peptide (pep-2 in FIG. 5) two oligomers were designed: ED-3*, 5'-ATG-GAC/T-AAC/T-GCN-GTN-GT-3' (SEQ ID NO:10 and SEQ ID NO:11) and ED-4*, 5'-GTI-GA(CT) T/C-TTI-ACI-CCI-CCI-GCG/T-TGG/A-TA-3' (SEQ ID NO:12 and SEQ ID NO:13).

6.1.5. CLONING OF THE ENDO-A GENE

Genomic DNA was isolated from *F. keratolyticus* by using the EASY DNA™ kit (Invitrogen) and was then dissolved in Tris-EDTA buffer, pH 7.4, to a final concentration of 0.9 mg/ml. By using the genomic DNA as a template and ED-1* and ED-4* as primers, a DNA fragment corresponding to the sequence between pep-1 and pep-2 was amplified in a hot-start PCR (Zhu and Goldstein, 1993, Gene 137:309–314). The PCR reaction mixture was maintained at 80° C. while adding Taq DNA polymerase. The reaction was then carried out for 35 cycles at 94° C. for 1 min, 50° C. for 2 min and 72° C. for 3 min. The 5'- and 3'-ends of the ENDO-A gene were isolated by using the PCR in vitro Cloning Kit according to a procedure recommended by the manufacturer (Takara Shuzo Co.). The EcoRI-cassette and SalI-cassette were used to amplify the 5' end and 3' end, respectively, of the ENDO-A gene.

6.1.6. IN VITRO TRANSLATION AND IMMUNOPRECIPITATION

PCR™II vector containing the ENDO-A insert was translated with the TNT coupled reticulocyte lysate system (Promega) according to manufacturer's instructions. RNA was transcribed using $T_7$ polymerase, and protein was translated in the presence of [$^{35}$S]methionine. Immunoprecipitation was carried out using antibody against *B. fragilis* Endo-β-galactosidase and protein A-sepharose CL-4B beads. After the precipitated proteins were subjected to SDS-PAGE, the gel was treated with Fluoro-Hance™ reagent and then exposed to Kodak film at −70° C. overnight.

6.2. RESULTS AND DISCUSSION

In order to isolate the gene encoding ENDO-A, four highly degenerate deoxy-oligonucleotides were designed based on the peptide sequences derived from ENDO-A purified from *F. keratolyticus*. These oligomers, ED-1* through ED-4*, were used as primers in the hot-start PCR procedure in the presence of the genomic DNA isolated from *F. keratolyticus*. Both primer pairs (ED-1* and ED-2*, ED-3* and ED-4*) amplified DNA fragments corresponding to the length of the two peptides, pep-1 and pep-2, respectively (refer to FIG. 2). Interestingly, a DNA fragment of approximately 240 bp was visualized in PCR by using ED-1* and ED-4* as primers. The 240 bp-fragment was then subcloned into a PCR11 vector and sequenced. The deduced amino acid sequence from this DNA fragment matched perfectly with peptides, pep-1 and pep-2, derived from purified protein, suggesting that the PCR generated fragment was a part of the gene encoding ENDO-A.

The next step was to isolate the upstream and downstream sequences from the 240 bp fragment. The technique of cassette PCR was employed, wherein a "cassette" is added to a restriction-digested DNA fragment. In order to locate the proper restriction enzyme sites flanking the ENDO-A gene, a Southern blot was prepared using genomic DNA cleaved with various restriction enzymes and a radioactively labeled 240 bp fragment as a probe. A single band of either 3.4 kb or 4.5 kb was visible when the genomic DNA was digested with EcoRI or SalI, respectively. Thus, these two restriction enzymes were chosen for the cassette PCR. Using ED-6 and ED-5 (FIG. 2) as 3'-primers (consecutively) and oligomers from the EcoRI cassette as 5'-primers, a 0.8 kb fragment was amplified which overlapped at its 3' end with the 240 bp-fragment. Similarly, by applying ED-7, ED-8 (FIG. 2) and a SalI-cassette, a 1.0 kb-fragment was isolated which overlapped at its 5' end with the 240 bp fragment. DNA analysis strongly indicated that these three fragments, 0.8 kb, 240 bp and 1.0 kb, should cover the entire coding sequence for ENDO-A.

In order to generate an intact ENDO-A gene and to verify the sequences obtained, a 1.4 kb-fragment was amplified from the F. keratolyticus genomic DNA using ED-11 and Ed-12 as primers (FIG. 2). This fragment was directly subcloned into a pCRII vector, generating the plasmid pCR-ED, for further characterization. As shown in FIG. 2, this 1.4 kb-DNA was found to contain a single open reading frame coding for a protein of 422 amino acid residues with a molecular mass of 45 kDa. Its authenticity was established by co-linearity of deduced amino acid sequence with seven peptides (underlined sequences in FIG. 2) isolated from purified ENDO-A. As indicated by N-terminal sequencing, the mature enzyme starts at position 47, suggesting that the nascent protein contains a leading peptide of 46 residues. This leading peptide, which has common characteristics for a prokaryotic secretion signal, is consistent with the observation that ENDO-A is synthesized and secreted into the F. keratolyticus culture medium. In addition, based on the DNA sequence, the mature ENDO-A has a molecular mass of 41 kDa, which closely resembles the molecular mass of ENDO-A purified from F. keratolyticus (FIG. 7) as estimated by SDS-PAGE analysis.

In vitro transcription and translation of ENDO-A

In order to further confirm that the cloned DNA encodes ENDO-A, it was subjected to transcription and translation using a cell-free reticulocyte lysate system (TNT) and $^{35}S$ labeled methionine. As is shown in FIG. 3, when the product of transcription/translation was combined with B. fragilis endo-β-galactosidase antibody, an immune precipitate was obtained which, when subjected to SDS-PAGE, yielded a major band in the region of the gel which was consistent with the molecular mass of mature ENDO-A plus the putative signal sequence (as based on the cDNA sequence).

Homology comparison

Although endo-β-galactosidase activity has been identified in a number of species, the sequence shown in FIG. 2 is believed to represent the first endo-β-galactosidase gene isolated to date. By applying a sequence homology search (BLAST) of available protein data base sequences, it was found that F. keratolyticus ENDO-A is homologous to glucan endo-1,3-b-glucosidase (EC 3.2.1.39) isolated from Bacillus circulars and endo-β-1,3-1.4-glucanase (EC 3.2.1.73) isolated from Rhodothermus marinus. Their sequence alignment of homology regions were demonstrated by CLUSTRALW Multiple Sequence Alignments (shown in FIG. 4). In the regions selected, ENDO-A demonstrates 40% and 41% of homology (alignment window) with glucan endo-1,3-β-glucosidase and endo-β-1,3-1,4-glucanase respectively, by using the program PROSIS (Hitachi Software Engineering). Although these three enzymes have distinctive substrate specificities they all belong to the endoglycosidase family, and may bear certain structural resemblances.

ENDO-A from F. keratolyticus and endo-β-galactosidase enzymes isolated from E. freundi and B. fragilis also appear to share homology at the protein level. This was determined by SDS-PAGE followed by Western blotting of the three enzymes with antibody prepared against the endo-β-isolated from B. fragilis. As shown in FIG. 5, all three enzymes gave a positive reaction with this antibody preparation even though the molecular weights of the endo-β-galactosidases from B. fragilis and E. freundi are significantly different from the molecular weight of ENDO-A.

Isolation and purification of ENDO-A

Purification procedures were performed at 4° C. and followed the methodology developed by Kitamikado et al (1980, J. Biol Chem. 256:3906–3909) with some modification. Briefly, the culture supernatant was first concentrated by ultrafiltration, and then its proteins were precipitated with ammonium sulfate at 80% saturation. The precipitate was dissolved and then subjected to various chromatographic procedures as summarized in Table 1. These included: size exclusion, anion/cation exchange and an immobilized reactive dye system. In addition, chromatofocusing was used as the final step in order to obtain the purity necessary for amino acid sequence analysis. This replaced Kitamikado's second-time use of DEAE Sephadex. This modification significantly helped to produce ENDO-A having a specific activity of 148, as compared to a specific activity of 44 for enzyme prepared by the published Kitamikado method. Furthermore, recovery was four times more efficient in the method utilizing chromatofocusing.

Aside from the chromatofocusing step, the other modifications of the Kitamikado procedure included concentrating the culture supernatant and increasing the amount of ammonium sulfate; both were needed in order to optimize recovery when dealing with large volumes. Samples from each step of the enzyme purification were analyzed by SDS-PAGE stained with Coomassie blue. As can been seen in FIG. 6, the final purification step yielded only one band indicating homogeneity of ENDO-A.

Two other significant differences were observed between isolated ENDO-A and Kitamikado et al's preparation. First, the molecular weight of ENDO-A (determined by SDS-PAGE) was approximately 43 Kd (FIG. 7), whereas Kitamikado's preparation exhibited a molecular weight (determined by Sepahadex G-200 chromatography) of about 30 Kd. Second, the isoelectric point of ENDO-A was found to be 6.9 (FIG. 8), whereas the isoelectric point of Kitamikado's preparation was 6.0.

TABLE I

Purification of Endo-β-Galactosidase from 100 L Culture Supernatant of
*Flavobacterium keratolyticus*

| Step Purification | Total Units | Total Protein (mg) | Specific Activity (Units/mg) | Recovery (%) | Fold |
|---|---|---|---|---|---|
| culture supernatant | 1132 | 107809 | 0.01 | 100 | 1 |
| concentrate | 1076 | 26 625 | 0.04 | 95 | 4 |
| (NH$_4$)$_2$SO$_4$ precipitation | 926 | 595 | 1.56 | 82 | 156 |
| Sephadex G-100 | 756 | 136 | 5.56 | 67 | 556 |

TABLE I-continued

Purification of Endo-β-Galactosidase from 100 L Culture Supernatant of *Flavobacterium keratolyticus*

| Step Purification | Total Units | Total Protein (mg) | Specific Activity (Units/mg) | Recovery (%) | Fold |
|---|---|---|---|---|---|
| CM-C-50/ DEAE-A-50 Sephadex Blue Sepharose | 702 | 22.8 | 30.79 | 62 | 3079 |
| Minor fraction | 52 | 17.8 | 2.92 | 4.6 | — |
| Major fraction | 433 | 4.5 | 96.2 | 38.3 | 9620 |
| Chromatofocusing (major fraction from Blue Seph.) | 505 | 3.4 | 148.5 | 44.6 | 14850 |

7. EXAMPLE: EXPRESSION OF RECOMBINANT ENDO-A

In order to demonstrate that the ENDO-A cDNA clone indeed encodes enzymatically active ENDO-A, the cDNA was subcloned into a number of expression vectors for its functional expression in different host systems. The plasmid pCR-ED, containing the ENDO-A cDNA downstream from the T7 promoter, was added to rabbit reticulocyte lysate for in vitro transcription and translation. The product was then assayed for the ENDO-A activity by using $^3$H-labeled glycopeptides as the substrate. As shown in Table II, the activity from the expression vector pCR-ED was 2021 (cpm), whereas the background level was only 803 (cpm) by using the vector pCRII as a control. Furthermore, the ENDO-A cDNA was subcloned into vectors pKK-233 and pLEX, generating pKK-ED and pLEX-ED, respectively. The plasmid pKK-ED, driven by the IPTG-inducible promoter, was transformed into the *E. coli* strain GI-724. The recombinant protein ENDO-A produced in both systems demonstrated the enzymatic activity towards the substrate keratan sulfate as indicated in Table II. This data thus confirms the authenticity of the cDNA clone encoding ENDO-A.

TABLE II

| Expression System | DNA plasmid | ENDO-A Activity | Substrate |
|---|---|---|---|
| In vitro transcription and translation | pCRII (control) | 803 cpm | $^3$H-labeled glycopeptides |
| | pCR-ED | 2021 cpm | $^3$H-labeled glycopeptides |
| IPTG induction IPTG induction in *E. coli* ABLE | pKK-233 (control) | 0.453 ($OD_{690}$) | keratan sulfate |
| | pKK-ED | 0.994 ($OD_{690}$) | keratan sulfate |
| Tryptophan induction in *E. coli* GI724 | pLEX (control) | 0.504 ($OD_{690}$) | keratan sulfate |
| | PLEX-ED | 1.257 ($OD_{690}$) | keratan sulfate |

8. DEPOSIT OF MICROORGANISMS

The following plasmid was deposited with the American Type Culture Collection (ATCC), 10801 University Boulevard Manassas, Va. 20110-2209, Aug. 28, 1996 pCR-ED, accession no. 97699.

Various publications are cited herein, the contents of which are hereby incorporated by reference in their entireties.

What is claimed is:

1. A purified and isolated nucleic acid encoding an endo-β-galactosidase from *Flavobacterium keratolyticus*.

2. A microorganism into which a nucleic acid according to claim 1 has been introduced.

3. A microorganism containing the nucleic acid of claim 1, wherein the microorganism is not *Flavobacterium keratolyticus*.

4. A vector containing the nucleic acid of claim 1.

5. A purified and isolated nucleic acid encoding ENDO-A, and having a sequence as set forth in FIG. 2 (SEQ ID NO:1).

6. A microorganism into which a nucleic acid according to claim 5 has been introduced.

7. A microorganism containing the nucleic acid of claim 5, wherein the microorganism is not *Flavobacterium keratolyticus*.

8. A vector containing the nucleic acid of claim 5.

9. A purified and isolated nucleic acid which is at least 30 base pairs in length and which hybridizes to the nucleic acid of claim 5 under stringent conditions.

10. A microorganism containing the nucleic acid of claim 9, wherein the microorganism is not *Flavobacterium keratolyticus*.

11. A vector containing the nucleic acid of claim 9.

12. A purified and isolated nucleic acid encoding ENDO-A, as prepared from the vector pCR-ED, as deposited with the American Type Culture Collection and assigned accession number 97699.

13. A microorganism containing the nucleic acid of claim 12, wherein the microorganism is not *Flavobacterium keratolyticus*.

14. A purified and isolated nucleic acid encoding ENDO-A, wherein ENDO-A has an amino acid sequence as set forth in FIG. 2 (SEQ ID NO:2).

15. A microorganism containing the nucleic acid of claim 14, wherein the microorganism is not *Flavobacterium keratolyticus*.

16. A method of producing endo-β-galactosidase comprising (i) introducing a nucleic acid encoding ENDO-A into a suitable host cell; (ii) culturing the host cell produced in step (i) under conditions compatible with expression of ENDO-A; and (iii) purifying ENDO-A from the culture produced in step (ii).

* * * * *